United States Patent

Imai et al.

Patent Number: 5,374,489
Date of Patent: Dec. 20, 1994

[54] ORGANIC ELECTROLUMINESCENT DEVICE

[75] Inventors: Kunio Imai, Tsurugashima; Takeo Wakimoto, Tsurugashima; Yasuhiko Shirota, Osaka; Hiroshi Inada, Kobe; Tomokazu Kobata, Kobe, all of Japan

[73] Assignees: Pioneer Electronic Corporation, Tokyo; Yasuhiko Shirota, Osaka; Bando Chemical Industries, Ltd., Kobe, all of Japan

[21] Appl. No.: 37,101

[22] Filed: Mar. 26, 1993

[30] Foreign Application Priority Data

Mar. 27, 1992 [JP] Japan .................... 4-71328
Mar. 22, 1993 [JP] Japan .................... 5-62074

[51] Int. Cl.$^5$ .............................. H05B 33/20
[52] U.S. Cl. ................... 428/690; 428/691; 428/917; 313/503; 313/504; 313/505; 313/506; 313/507; 313/508; 313/509
[58] Field of Search ............ 428/690, 691, 917; 313/503–509

[56] References Cited

FOREIGN PATENT DOCUMENTS

0508562A1 10/1992 European Pat. Off. .
0517542A1 12/1992 European Pat. Off. .

OTHER PUBLICATIONS

European Search Report dated Dec. 8, 1993.
Adv. Mater. 3(1991) No. 11 pp. 549–550 Higuchi et al.
J. Phys. Chem. (97) 6-10-93 No. 23 pp. 6240–6247 Naito et al.

*Primary Examiner*—Charles R. Nold
*Attorney, Agent, or Firm*—Fish & Richardson

[57] ABSTRACT

An organic electroluminescent device having an organic emitting layer and a hole transport layer laminated with each other and arranged between a cathode and an anode, and the hole transport layer is made of tris-phenothiazinyl-triphenylamine or tris-phenoxazinyl-triphenylamine derivative. The hole transport layer has a high heat-resistant property and high conductivity to improve durability and emits light at a high luminance and a high efficiency upon application of a low voltage.

2 Claims, 1 Drawing Sheet

ORGANIC ELECTROLUMINESCENT DEVICE

BACKGROUND OF THE INVENTION

1. Field of the invention

The present invention relates to an electroluminescent (EL) device having an emitting layer made of an emitting substance, which utilizes an electroluminescence phenomenon that the emitting substance emits light by applying an electric current to the emitting layer. More particularly, it is concerned with an organic EL device in which the emitting layer is made of an organic emitting substance.

2. Description of the prior art

As prior art organic EL devices, there have been known a device of a two-layer structure having two layers of organic compounds as shown in FIG. 1, in which an organic fluorescent thin film 3 (hereinafter referred as "emitting layer") and an organic hole transport layer 4 are laminated with each other and are arranged between a metal cathode 1 and a transparent anode 2. There have been also known a device of three-layer structure having three layers of organic compounds as shown in FIG. 2, in which an organic electron transport layer 5, an emitting layer and an organic hole transport layer 4 are laminated in sequence and are sandwiched as a whole between a metal cathode 1 and a transparent anode 2. The hole transport layer 4 facilitates the infusion of the holes from the anode and blocks electrons. The electron transport layer 5 facilitates the infusion of electrons from the cathode.

In these organic EL devices, a glass substrate 6 is furnished outside the transparent anode 2. The recombination of electrons infused from the metal cathode 1 and the holes infused from the transparent anode 2 to the emitting layer 3 generates excitons. The excitons emit light when they are deactivated through radiation. This light radiates toward the outside through the transparent anode 2 and the glass substrate 6.

The conventional organic EL devices constructed as indicated above generally emit light even at a low voltage. However, when the EL device with a simple matrix structure is continuously driven by a DC current, its luminance is likely to deteriorate and then the EL device easily becomes destructible. The heat resistance of such a device is also low.

SUMMARY OF THE INVENTION

An object of the present invention is to provide an organic EL device with a high heat resistance capable of stably emitting light at a high luminance and a high efficiency for a long time to overcome the above mentioned problem.

An organic EL device according to a first aspect of the present invention comprises a cathode, an emitting layer of an organic compound, a hole transport layer of an organic compound and an anode which are laminated in sequence, wherein said organic compound of said hole transport layer is made of a tris-phenothiazinyl-triphenylamine derivative represented by the following chemical formula (1)

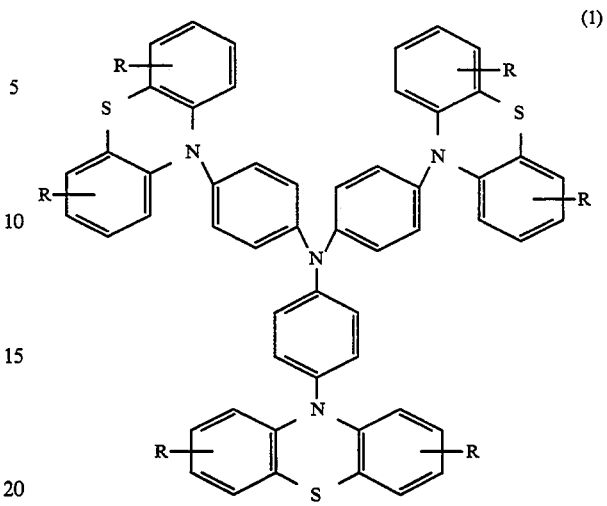

where R each independently represents a hydrogen atom, an alkyl group of from 1 to 6 carbon atoms, a halogen group, a cyano group, a nitro group, a primary, secondary or tertiary amino group, an aryl group of from 6 to 14 carbon atoms, an aralkyl group or an alkoxy group.

An organic EL device according to a second aspect of the present invention comprises a cathode, an emitting layer of an organic compound, a hole transport layer of an organic compound and an anode which are laminated in sequence, wherein said organic compound of said hole transport layer is made of a tris-phenoxazinyl-triphenylamine derivative represented by the following chemical formula (2)

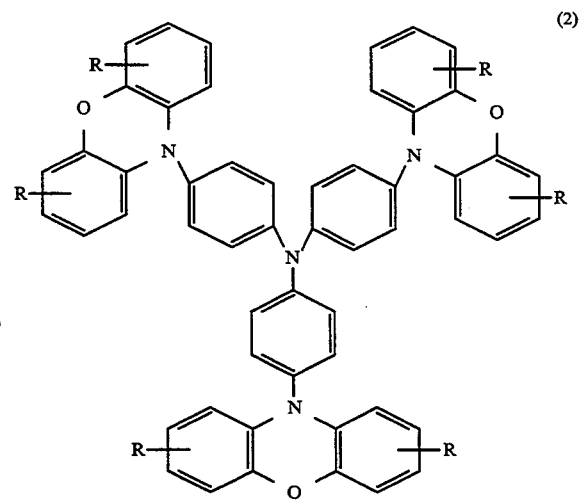

where R each independently represents a hydrogen atom, an alkyl group of from 1 to 6 carbon atoms, a halogen group, a cyano group, a nitro group, a primary, secondary or tertiary amino group, an aryl group of from 6 to 14 carbon atoms, an aralkyl group or an alkoxy group.

According to the present invention, there is obtained an organic EL device with a high heat resistance capable of stably emitting light at a high luminance and a high efficiency with the durability.

DETAILED DESCRIPTION OF PREFERRED EMBODIMENTS

The embodiments according to the present invention will be described in more detail with reference to the accompanying drawings.

Figure 1:
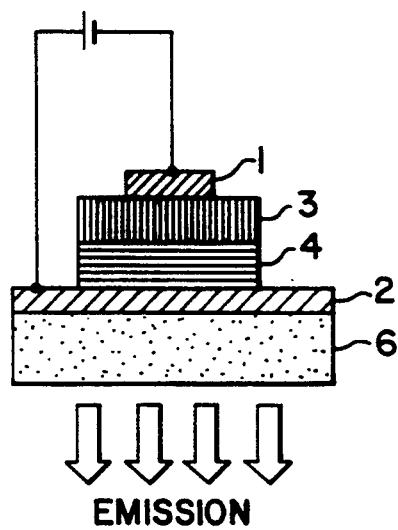
FIG. 1 is a schematic diagram showing an organic EL device with a two-layer structure.
Figure 2:
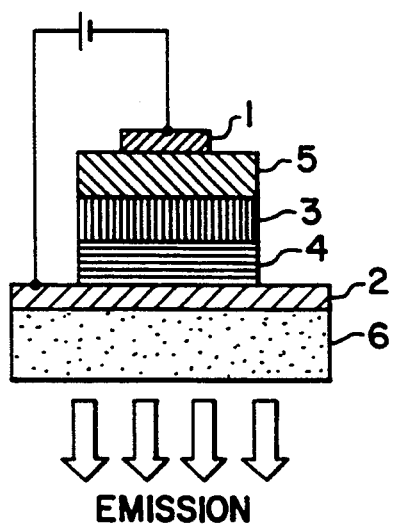
FIG. 2 is a schematic diagram showing an organic EL device with a three-layer structure.

The EL device in accordance with the present invention is similar to the organic EL device of the structure shown in FIG. 1 or 2. Such an EL device may have the two-layer structure formed by layering a fluorescent emission layer 3 and a positive-hole transport layer 4 between a pair of a metal cathode 1 and a transparent anode 2 as shown FIG. 1. The EL device also may have the three-layer structure formed by layering an organic electron transport layer 5, the organic fluorescent film 3 and the organic positive-hole transport layer 4 in sequence between a pair of the metal cathode 1 and the transparent anode 2. In the both structures of the EL device, at least one of the electrodes 1 and 2 may be transparent. The cathode 1 is formed of a metal with a lower work function such as aluminum, magnesium, indium, silver or alloys of the individual metals thereof in the thickness range of from about 100 to 5000 angstroms. The transparent anode 2 is formed of an electric conductive material with a higher work function such as indium-tin oxide (ITO) in the thickness range of from about 1000 to 3000 angstroms. Alternatively, the transparent anode 2 may be formed of gold with the thickness of from about 800 to 1500 angstroms. The electrode of gold thin film is semitransparent.

The hole transport layer 4 is made of a tris-phenothiazinyl-triphenylamine derivative represented by the above mentioned chemical formula (1).

Preferred examples of the tris-phenothiazinyl-triphenylamine derivative include 4, 4', 4''-tri(N-phenothiazinyl)triphenylamine (hereinafter referred as "TPTTA") denoted by the following formula (3):

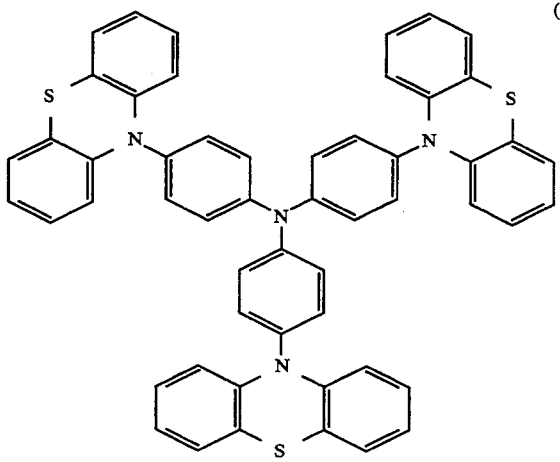

(3)

Alternatively, the hole transport layer 4 is made of a tris-phenoxazinyl-triphenylamine derivative represented the above mentioned chemical formula (2).

Preferred examples of the tris-phenoxazinyl-triphenylamine derivative includes 4, 4', 4''-tri(N-phenoxazinyl) triphenylamine (hereinafter referred as "TPOTA") denoted by the following formula (4):

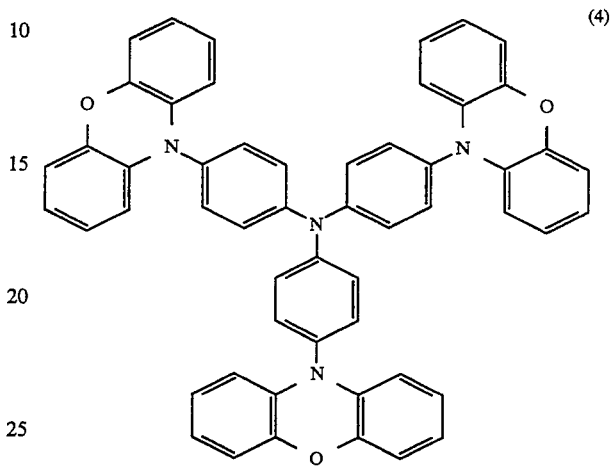

(4)

Inventors have produced so-called star-burst molecules which have a stellar structure, e.g. 4,4',4''-tris[N-(3-methylphenyl)-N-phenylamino]triphenylamine (hereinafter referred as "MTDATA") and 4,4',4''-tris(N,N-diphenylamino) triphenylamine (hereinafter referred as "TDATA") in order to obtain an amorphous molecular material having a photoelectric function. Inventors have studied the morphological changes, electric properties and photoelectric characteristics with respect to these star-burst molecules. Inventors have further synthesized TPTTA by using phenothiazine and TPOTA by using phenoxazine which are pi electron conjugate molecules, and studied their various properties and then revealed that each of these star-burst molecules has a high glass transition point and a high molecular stiffness.

TPTTA was synthesized from 4, 4', 4''-triiodo-triphenylamine and phenothiazine through the Ullmann reaction. The identification of TPTTA is conducted by the various spectrum and ultimate analyses.

Synthesized TPTTA was heated and melted to be an isotropic solution and then allowed to cool for a time undisturbed and to become a transparent glass. This glass was allowed to stand for one year at a room temperature to be stably maintained the glass phase per se. In the differential scanning calorimetry (DSC) of such a TPTTA sample, the glass transition phenomenon from the glass phase to the superclooled phase was observed at 141° C. and after that, the exothermic peak of 197° C. due to the crystallization thereof and then the endothermic peak of 288° due to melting were measured while being raised continuously the temperature.

TPOTA was similarly synthesized from 4, 4', 4''-triiodo-triphenylamine and phenoxazine through the Ullmann reaction and measured in the DSC as well as TPTTA. In the DSC curve of TPOTA, the glass transition temperature of 145° C., the exothermic peak of 176° C. due to the crystallization thereof and the endothermic peak of 341° C. due to melting were measured.

Table 1 shows the glass transition temperatures of TDATA, MTDATA, TPTTA and TPOTA. TPTTA and TPOTA have respectively glass transition temperatures higher than those of TDATA and MTDATA.

TABLE 1

| Samples | TDATA | MTDATA | TPTTA | TPOTA |
|---|---|---|---|---|
| Glass transition temperature Tg (°C.) | 83 | 75 | 141 | 145 |

It is assumed that the high glass transition points of the TPTTA and TPOTA are obtained due to the increase of molecular stiffness of these star-burst molecules caused by linking the outside phenyl groups with chalcogen atoms. This result shows that the glass transition point of the star-burst molecule can be controlled by the change of molecular stiffness thereof.

The tris-phenothiazinyl-triphenylamine derivative such as TPTTA and the tris-phenoxazinyl-triphenylamine derivative such as TPOTA have heat-resistant properties of high melting points and glass transition points in the amorphous states respectively. Also, each of tris-phenothiazinyl-triphenylamine derivative and tris-phenoxazinyl-triphenylamine derivative has a twisted molecular structure and three dimensional frameworks. Thus, these triphenylamine derivatives of a star-burst molecule are hardly crystallized and have excellent shielding properties against a surface of another substance. Even when a thin film made of one of such triphenylamine derivatives is left at the temperature lower than room temperature for several months, it is not crystallized. Therefore each triphenylamine derivative film in an amorphous maintains its excellent thin film forming property. These derivatives are capable of being used as the transport layer materials desirable for forming emitting layer 3 thereon.

In addition, another preferable example of tris-phenothiazinyl-triphenylamine derivative is 4, 4', 4"-tris(3-methyl-N-phenothiazinyl) triphenylamine denoted by the following formula:

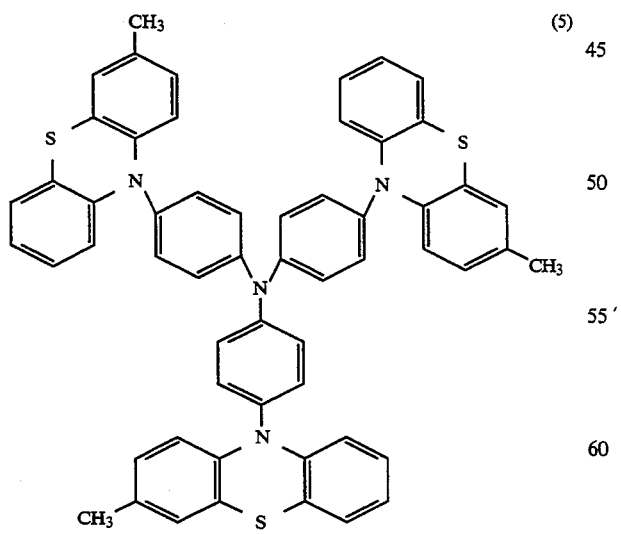
(5)

and another preferable example of tris-phenoxazinyl-triphenylamine derivative is 4, 4', 4"-tris(3-methyl-N-phenoxazinyl) triphenylamine denoted by the following formula:

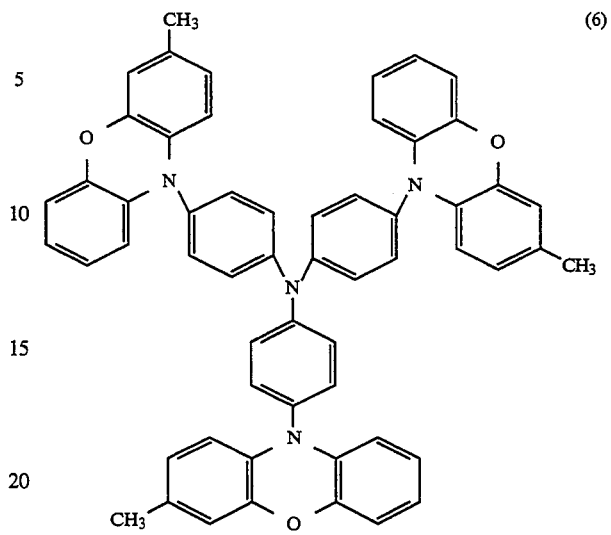
(6)

The present invention is not restricted to these examples mentioned above.

The emitting layer 3 of the organic EL device comprises the organic fluorescent compound. Preferred examples of the compound are Aluminum oxine chelate (hereinafter referred as "Alq3") denoted by the following formula 7 and, tetraphenylbutadiene (TPB) derivatives respectively represented by the following chemical formulas 8 to 10, which may include another fluorescent compound as an additional material. The thickness of the emitting layer 3 is within 1 micron meter or less. In addition, other preferred examples used for the emitting layer 3 are represented by the following formulas 11 to 15:

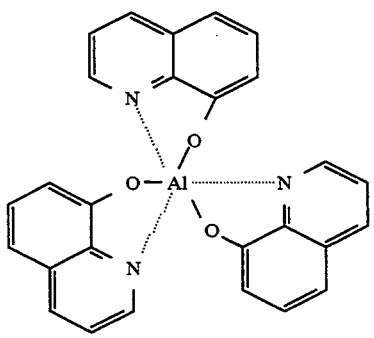
(7)

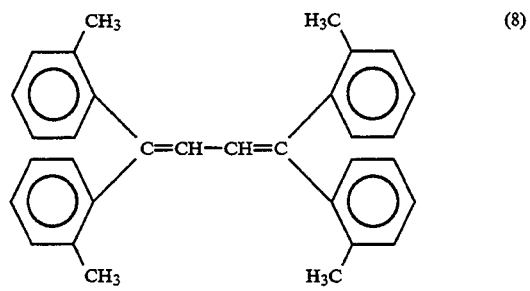
(8)

-continued

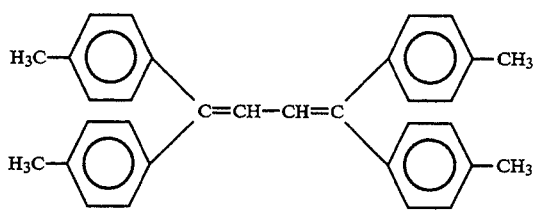 (9)

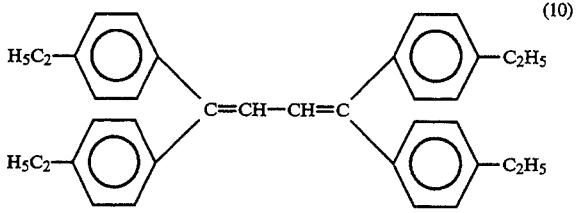 (10)

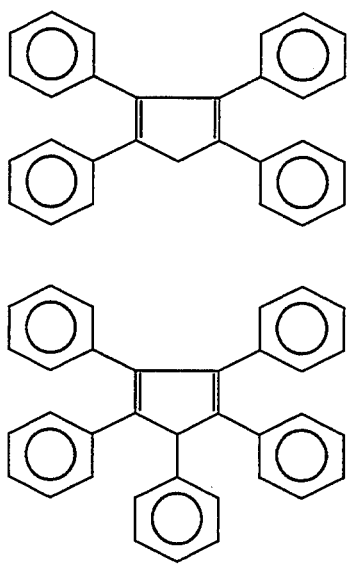

(11)

(12)

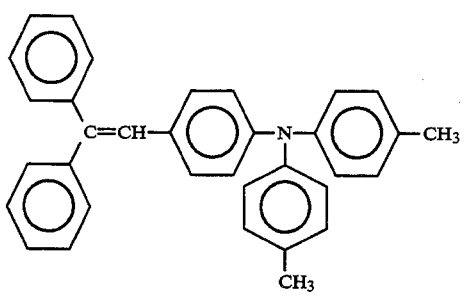 (13)

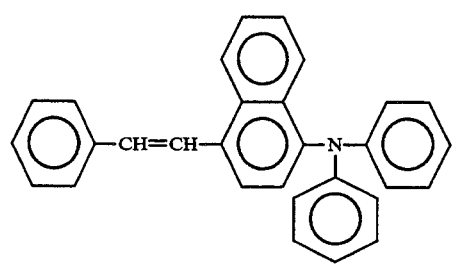 (14)

-continued

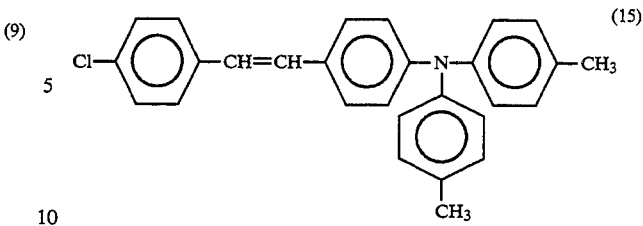 (15)

When the organic EL device has the three-layer structure, the electron transport layer 5 is preferably made of Bu-PBD [2-(4'-tert-butylphenyl)-5-(biphenyl)-1,3,4-oxadiazole] represented by the following chemical formula 16. Examples of suitable organic compounds which may be employed as the electron transport layer 5 are represented by the following chemical formulas 17 to 23.

(16)

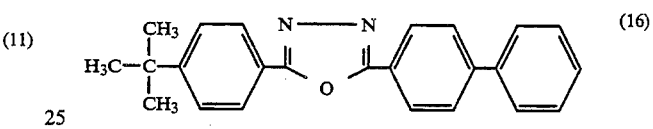 (17)

(18)

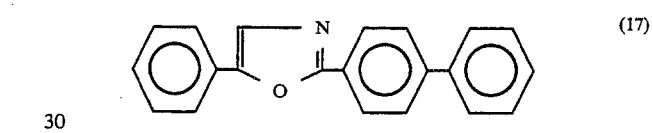 (19)

(20)

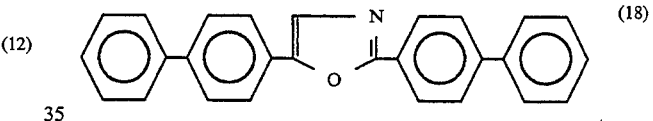 (21)

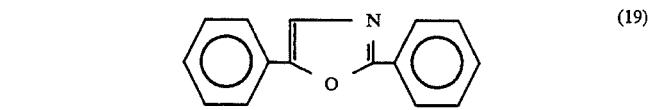 (22)

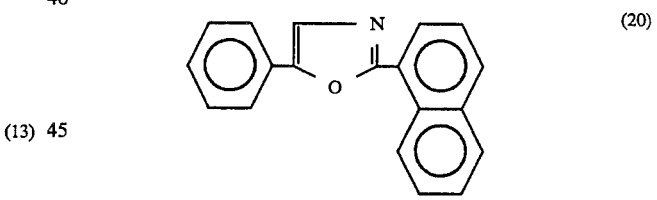 (23)

(EXAMPLE 1)

A glass substrate on which an anode of ITO had been formed at 2000 Å thick, was prepared. First, TPTTA of formula 3 was deposited on the ITO anode with the thickness of 500 Å as a hole transport layer at the vacuum deposition rate of 4 Å/sec. Next, Al$_{q3}$ of formula 7 was deposited on the TPTTA layer as an emitting layer with the thickness of 500 Å at the vacuum deposition rate of 5 Å/sec. Then, magnesium and aluminum were vacuum co-deposited on the emitting layer of Al$_{q3}$ with the thickness of 1500 Å at the atomic ratio of Mg:Ag=10:1 as a cathode. Each of these thin films was formed by a vacuum deposition method at vacuum conditions equal to or less than $1.0 \times 10^{-5}$ Torr.

When the resultant EL device as shown in FIG. 1 was operated with the application of the DC voltage 9 V at the constant current density of 6.3 mA/cm$^2$ the emission of this EL device had a luminance of 173 cd/m$^2$. Upon application of the DC voltage at the constant current density of 6.3 mA/cm$^2$, the half-life of the initial luminance of this EL device was 385 hours under a vacuum state.

There was hardly changed in the current and luminance property before and after the heat-resistance test in which the EL device of example 1 was stored at the temperature of 90° C. for 72 hours under a vacuum state.

(EXAMPLE 2)

An EL device was assembled by the same procedure as in the Example 1, except that the transport layer was made of TPOTA represented by formula 4 instead of TPTTA used in the Example 1

When the resultant EL device was operated with the application of the DC voltage 8V at the constant current density of 6.3 mA/cm$^2$, the emission of this EL device had a luminance of 152 cd/m$^2$. Upon application of the DC voltage at the constant current density of 11 mA/cm$^2$, the half-life of the initial luminance of this EL device was 370 hours under a vacuum state.

There was hardly changed in the current and luminance property before and after the heat-resistance test in which the EL device of example 2 was stored at the temperature of 90° C. for 72 hours under a vacuum state.

(EXAMPLE 3)

Figure 3:
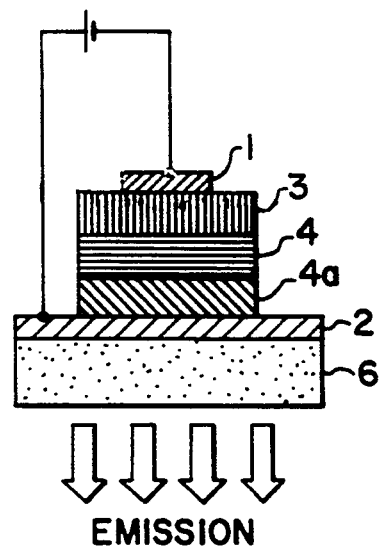
FIG. 3 is a schematic diagram showing an organic EL device shown in Examples 3 and 4 in accordance with the present invention.

An EL device shown in FIG. 3 was assembled by the same procedure as in the Example 1, except that a second transport layer 4a made of MTDATA at a thickness 500 Å was formed between the ITO anode and the TPTTA transport layer whose thickness was 250 Å layer.

When the resultant EL device was operated with the application of the DC voltage 9V at the constant current density of 6.3 mA/cm$^2$, the emission of this EL device had a luminance of 252 cd/m$^2$. Upon application of the DC voltage at the constant current density of 7.5 mA/cm$^2$, the half-life of the initial luminance of this EL device was 550 hours under a vacuum state.

In this way, this example EL device having a multilayer of the second transport layer of MTDATA and the TPTTA transport layer has a luminance efficiency higher than that of the example 1 and a long-life luminance.

(EXAMPLE 4)

An EL device as shown in FIG. 3 was assembled by the same procedure as in the Examples 1 and 3, except that the transport layer was made of TPOTA instead of TPTTA used in the Example 3.

When the resultant EL device was operated with the application of the DC voltage 9 V at the constant current density of 6.3 mA/cm$^2$, the emission of this EL device had a luminance of 218 cd/m$^2$. Upon application of the DC voltage at the constant current density of 8.5 mA/cm$^2$, the half-life of the initial luminance of this EL device was 530 hours under a vacuum state.

In this way, this example EL device having a multilayer of the second transport layer of MTDATA and the TPOTA transport layer has a luminance efficiency higher than that of the example 2 and a long-life luminance.

(Comparative Example)

An EL device was assembled by the same procedure as in the Example 1, except that the transport layer was made of N, N'-diphenyl-N-N'-bis(3-methylphenyl)-1,1'-biphenyl-4,4'-diamine (so-called "TPD") represented by the following chemical formula (24) instead of TPTTA used in the Example 1.

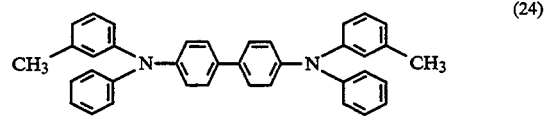

(24)

When the resultant EL device was operated with the application of the DC voltage 6 V at the constant current density of 6.3 mA/cm$^2$ the emission of this EL device had a luminance of 258 cd/m$^2$. Upon application of the DC voltage at the constant current density of 7.5 mA/cm$^2$, the half-life of the initial luminance of this EL device was 131 hours under a vacuum state.

The current and luminance property largely changed between before and after the same heat-resistance test of example 1, the deterioration of luminance of the EL device was rapid in comparison with the examples mentioned above.

As described above, the organic EL device according to the present invention comprises the organic emitting layer and the first organic hole transport layer laminated with each other and arranged between the cathode and the anode. The hole transport layer is made of tris-phenothiazinyl-triphenylamine or tris-phenoxazinyl-triphenylamine derivative. The hole transport layer has a high heat resistant property. Thus, the hole transport layer reduces the undesirable influence thereon caused by the heat generated from application of electric current. In this way, it is possible according to the present invention to improve the durability of the organic EL device which emits light at a high luminance and a high efficiency upon application of a low voltage.

What is claimed is:

1. An organic electroluminesent device comprising a cathode, an emitting layer of an organic compound, a hole transport layer of an organic compound and an anode which are laminated in sequence, wherein said organic compound of said hole transport layer is made of a tris-phenoxazinyl-triphenylamine derivative represented by the following chemical formula

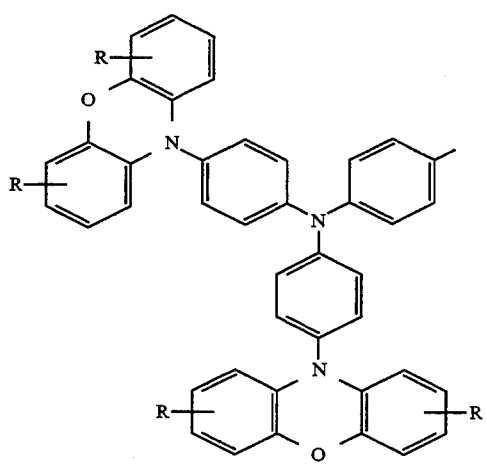

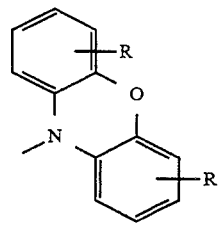

where R each independently represents a hydrogen atom, alkyl group of from 1 to 6 carbon atoms, a halogen group, a cyano group, a nitro group, a primary, secondary or tertiary amino group, an aryl group of from 6 to 14 carbon atoms, an aralkyl group or an alkoxy group.

2. An organic electroluminescent device according to claim 1, wherein an organic electron transport layer is provided between said cathode and said emitting layer.

* * * * *